United States Patent [19]

Barchas et al.

[11] Patent Number: 4,613,586

[45] Date of Patent: Sep. 23, 1986

[54] GASTRIN RELEASING PEPTIDE-LIKE PEPTIDES

[75] Inventors: Jack D. Barchas, Stanford; Eckard Weber, San Francisco; Christopher J. Evans, Redwood City; Jaw-Kang Chang, San Carlos, all of Calif.; Robin G. Lorenz, Okeene, Okla.; Kevin A. Roth, Mountain View, Calif.

[73] Assignee: Board of Trustees of the Leland Stanford Junior University, Stanford, Calif.

[21] Appl. No.: 602,116

[22] Filed: Apr. 19, 1984

[51] Int. Cl.$^4$ .................. A61K 17/43; C07K 7/06; C07K 7/08

[52] U.S. Cl. .................................. 514/13; 514/15; 530/326

[58] Field of Search .............. 260/112.5 R; 514/13, 514/15

[56] References Cited

U.S. PATENT DOCUMENTS 4,207,311 6/1980 Brown et al. ............... 260/112.5 R
4,331,661 5/1982 Marki et al. ................ 260/112.5 R

OTHER PUBLICATIONS

Biochem. and Biophys. Res. Commun. vol. 90, No. 1, (1979) 227-233, McDonald, et al..
Biochem. and Biophys. Res. Commun. vol. 112, No. 2, (1983) 528-536.

*Primary Examiner*—Delbert R. Phillips
*Attorney, Agent, or Firm*—Flehr, Hohbach, Test, Albritton & Herbert

[57] ABSTRACT

Novel peptides having gastrin releasing peptide-like activity having the structures Ala-Pro-Val-Ser-Val-Gly-Gly-Gly-Thr-Val-Leu-Ala-Lys-Met-Tyr-Pro-NH$_2$ and Gly-Asn-His-Trp-Ala-Val-Gly-His-Leu-Met-NH$_2$, have been isolated from rat and guinea pig brain extracts and synthesized by a solid phase peptide synthesis methods. The GRP-like peptides are useful as pharmaceuticals to lower body temperature, increase respiratory activity, reduce food intake, stimulate pancreatic hormone release, stimulate pituitary hormone release and suppress thyroid hormone release in mammals.

16 Claims, 3 Drawing Figures

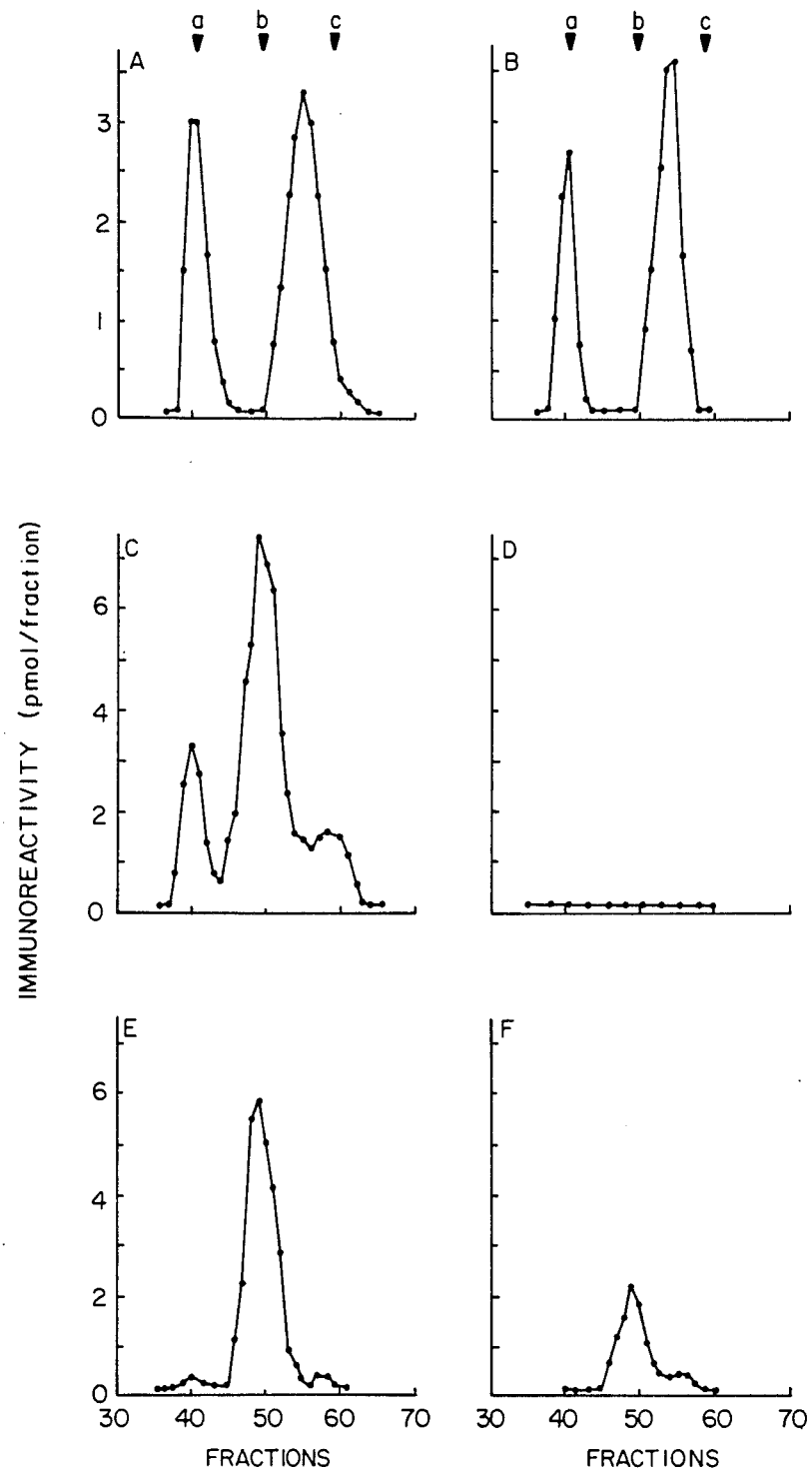
FIG.—1

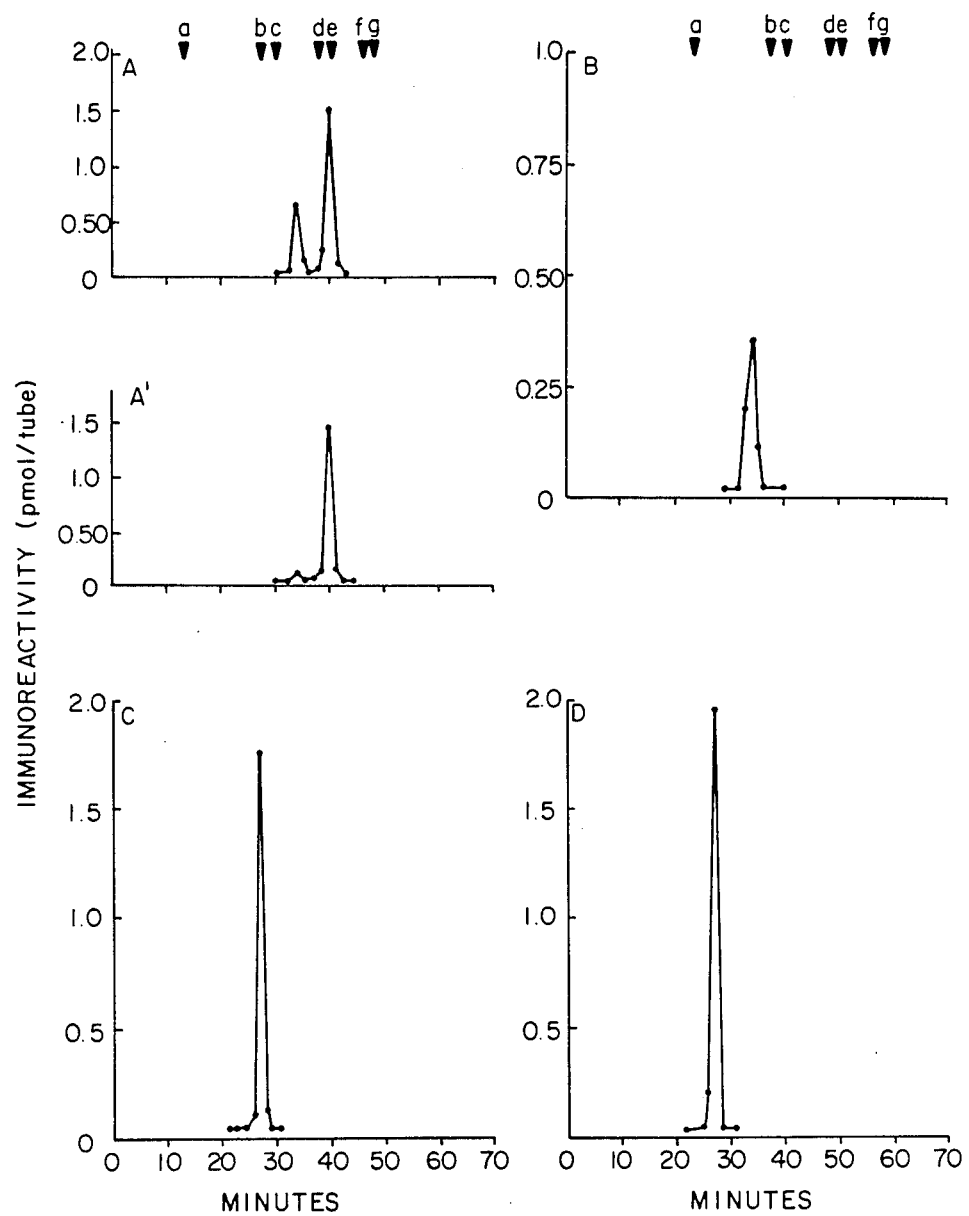
FIG.—2

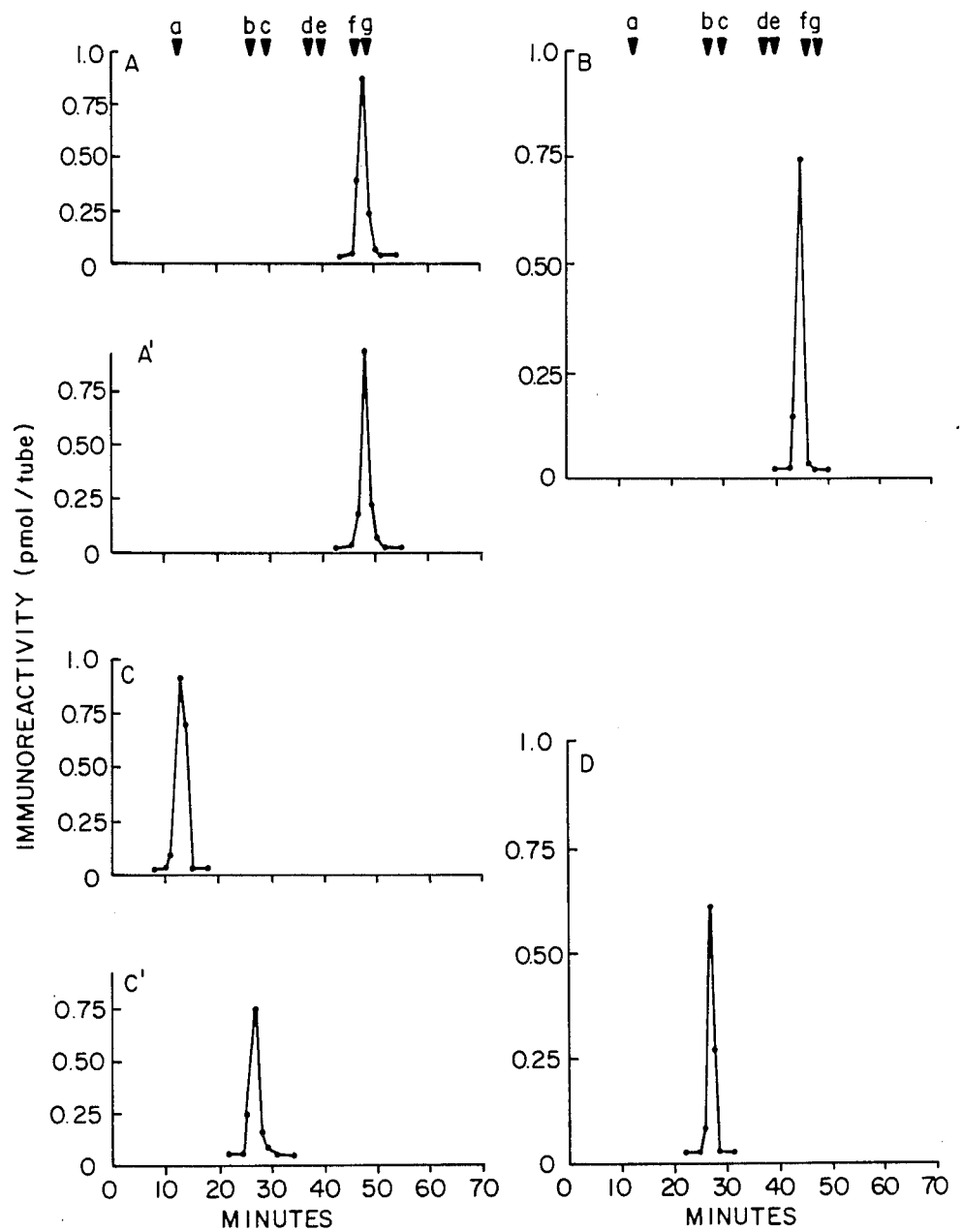
FIG.—3

GASTRIN RELEASING PEPTIDE-LIKE PEPTIDES

The United States Government has rights in this invention pursuant to Contract No. N00014-79-C-0796 and Grant MH23861 awarded by the Office of Naval Research and the National Institute of Mental Health.

The present invention is directed to a novel peptide having gastrin releasing peptide-like activity.

Recent studies have identified peptides in mammalian brain that are immunologically similar to bombesin, a tetradecapeptide isolated from amphibian skin. (Anastasi, A., Erpsamer, V., and Bucci, M., *Experientia* 27, 166–167 (1971)). Because bombesin, when injected into the brain, has potent effects on thermoregulation, eating and anterior pituitary hormone release, it has been suggested that it may be a peptide neurotransmitter or neuromodulator in mammalian nervous systems. (Brown, M., Rivier, J., and Vale, W., *Science* 196, 998–1000 (1977); Gibbs, J., Fauser, D. J., Rowe, E. A., Rolls, B. J., Rolls, E. T., and Maddison, S. P., *Nature* 282, 208–210 (1979); Rivier, C., Rivier, J., and Vale, W., *Endocrinology* 102, 519–522 (1978); Brown, M., Allen, R., Villarreal, J., Rivier, J., and Vale, W., *Life Science* 23, 2721–2728 (1978); and Moody, T. W., Pert, C., Rivier, J., and Brown, M. R., *Proc. Natl. Acad. Sci. USA* 75, 5372–5376 (1978)). No precise information regarding the exact molecular nature of the bombesin immunoreactive material in mammalian tissues is available although some evidence has been presented that brain bombesin behaves similarly to authentic bombesin in several chromatography systems. (Moody, T. W., O'-Donohue, T. L., and Jacobowitz, D. M., *Peptides* 2, 75–79 (1981)).

A 27 amino acid peptide has been isolated from porcine gut with a heptapeptide sequence at the carboxyterminus that is identical to the carboxyterminal seven amino acids of bombesin. (McDonald, T. J., Jornvall, H., Nilsson, G., Vagne, M., Ghatei, M., Bloom, S. R., and Mutt, V. *Biochem. Biophys. Res. Commun.* 90, 227–233 (1979). This 27 amino acid peptide stimulates the release of gastrin from the stomach mucosa and has been termed gastrin releasing peptide (GRP). GRP has the following formula:

Ala-Pro-Val-Ser-Val-Gly-Gly-Gly-Thr-Val-Leu-Ala-Lys-Met-Tyr-Pro-Arg-Gly-Asn-His-Trp-Ala-Val-Gly-His-Leu-Met-NH$_2$

Immunohistochemical studies have shown that GRP-like immunoreactive material is present in various regions of the rat brain where it is often colocalized with bombesin related immunoreactive material in the same neurons. (Roth, K. A., Weber, E., and Barchas, J. D. *Brain Research* 251, 277–282 (1982)). The present invention demonstrates that authentic bombesin is not present in guinea pig or rat brain and that the bombesin related material is a 10 amino acid carboxyterminal fragment of a GRP-like peptide (hereinafter GRP(18–27)-like peptide). (Roth, K. A., Evns, C. J., Lorenz, R. G., Weber, E., Barchas, J. D., Chang, J-K, *Biochem. Biophys. Res. Commun.* 112, 528–536 (1983)).

It is an object of the present invention to provide novel peptides having gastrin releasing peptide-like activity.

It is a further object of the present invention to provide methods for isolating and preparing novel peptides having gastrin releasing peptide-like activity.

It is another object of the present invention to provide pharmaceutical compositions useful for lowering body temperature, increasing respiratory activity, reducing food intake or suppressing appetite, stimulating pancreatic hormone release, stimulating pituitary hormone release, and suppressing thyroid hormone release in mammals.

FIG. 1 shows gel-filtration chromatography profiles of GRP carboxy terminal (A,B), GRP amino terminal (C,D), and GRP (1–16) carboxy terminal (E,F) immunoreactivity in guinea pig brain (A,C,E) and rat brain (B,D,F).

FIG. 2 shows reverse phase high performance liquid chromatography profiles of the lower molecular weight (MW) GRP immunoreactive peaks from gel filtration of guinea pig and rat brain.

FIG. 3 shows reverse phase high performance liquid chromatography profiles of the larger molecular weight (MW) GRP immunoreactive peak from gel filtration of guinea pig and rat brain.

The present invention provides biologically pure polypeptides having the formulas:

Ala-Pro-Val-Ser-Val-Gly-Gly-Gly-Thr-Val-Leu-Ala-Lys-Met-Tyr-Pro-NH$_2$ peptide (hereinafter GRP(1–16)-like peptide); and Gly-Asn-His-Trp-Ala-Val-Gly-His-Leu-Met-NH$_2$ (hereinafter GRP(18–27)-like peptide).

These peptides may be isolated from rat and guinea pig brain extracts, detected by radioimmunoassay and purified to homogeneity by gel filtration and reverse phase high performance liquid chromatography. The peptides of the present invention can be synthesized by solid phase peptide synthesis methods.

The peptides according to the present invention may be useful as pharmaceuticals to lower body temperature, increase respiratory activity, reduce food intake or suppress appetite, stimulate pancreatic hormone release, stimulate pituitary hormone release and suppress thyroid hormone release in mammals.

EXAMPLE 1

Isolation and Characterization of GRP(1–16) and (18–27)-Like Peptides

The GRP immunoreactive material from rat and guinea pig brain was characterized by gel filtration and reverse phase high performance liquid chromatography (RP-HPLC). Whole brains (without cerebellums) from 15 rats and from 10 guinea pigs were extracted in acid acetone (acetone:water:12N HCl; 40:6:1). Acid acetone extracts of rat brains and guinea pig brains were delipidized with heptane (as described by Weber, E., Evans, C. J., and Barchas, J. D., *Nature* 299, 77–79 (1982)), evaporated under nitrogen and resuspended in 2 ml of 50 percent acetic acid and placed on a 120×2.5 cm Sephadex G-50 column and eluted with 50 percent acetic acid. 5 ml fractions were collected and aliquots were evaporated under reduced pressure and assayed in three GRP RIA's, prepared as follows.

Three GRP antisera were generated in rabbits against synthetic porcine GRP and GRP(1–16) (Peninsula Laboratories, San Carlos, CA) linked by a water soluble carbodiimide to bovine throglobulin (as described by Weber, E., Evans, C. J., Chang, J-K. and Barchas, J. D., *J. Neurochem* 38, 436–447 (1982). RIA conditions have been described in Weber, E., Evans, C. J., and Barchas, J. D., *Nature* 299, 77–79 (1982). Three GRP RIA's were utilized, the specificity of these RIA's is indicated in Table 1.

TABLE 1

Crossreactivity of Gastrin Releasing Peptide Radioimmunoassays Percent Crossreactivity in RIA

| Synthetic Peptide | GRP(1–27) Code R3-2 | GRP(1–16) Code R2-6A | GRP(1–16) Code R2-6B |
|---|---|---|---|
| GRP | 100 | 100 | 03 |
| GRP(1–13) | 0 | 100 | 03 |
| GRP(1–16) | 0 | 100 | 100 |
| GRP(18–27) | 60 | 0 | 0 |
| α-N—acetyl-GRP(20–27) | 60 | 0 | 0 |
| Bombesin | 30 | 0 | 0 |

The GRP carboxyterminal antiserum crossreacted with GRP, GRP(18–27), and bombesin but not GRP(1–16). The GRP aminoterminal RIA crossreacted with GRP, GRP(1–13), GRP(1–16), but not GRP(18–27). The GRP(1–16) carboxyterminal antisera crossreacted with GRP(1–16) but had little crossreactivity with GRP, or GRP(1–13).

An antisera dilution of 1:20,000 for the GRP(1–27) R3-2 antisera and a dilution of 1:15,000 for the GRP(1–16) R2-6A were used for RIA. For these RIA's GRP(1–27) was used as $^{125}$I-trace and standard. An antisera dilution of 1:20,000 for GRP(1–16) R2-6B and GRP(1–16) trace and standard were used in the GRP(1–16) carboxyterminal assay. Crossreactivity was based on the amount of unlabeled peptide needed to obtain a 50 percent displacement of $^{125}$I-trace from the antisera. The highest concentration of unlabeled peptide tested was 1 μM.

The synthetic peptides were synthesized by standard solid phase methods and purified by gel-filtration and partition chromatography. Purity of the peptides was shown by RP-HPLC and amino acid analysis. GRP(18–27) was made by trypsin digestion of GRP(14–27) followed by RP-HPLC purification. GRP(1–13) was generated by trypsin digestion of GRP(1–16) followed by RP-HPLC purification.

After radioimmunoassay, aliquots of the immunoreactive peak fractions from the rat and guinea pig brain extracts were subjected to RP-HPLC analysis (as described in Weber, E., Evans, C. J., and Barchas, J. D., Nature 299, 77–79 (1982)). The large molecular weight (hereinafter MW) peak of GRP carboxyterminal immunoreactivity in rat and guinea pig brain was also trypsin digested prior to RP-HPLC. For trypsinization aliquots from the large MW peak were evaporated under nitrogen and resuspended in 500 μl of 0.2M Tris/HCl buffer pH 8.1. About 10,000 cpm of $^{125}$I-dynorphin and 10 μl of 1 mg/ml TPCK treated trypsin (Millipore) were added. The $^{125}$I-dynorphin served both as an internal standard for the chromatography and as a marker for monitoring the completeness of the trypsin digestion. The reaction was stopped after 2 hours by addition of 100 μl of glacial acetic acid and the sample injected on the column. HPLC fraction aliquots were evaporated under reduced pressure and analyzed by RIA.

Referring to FIG. 1, the gel-filtration chromatography profiles of GRP carboxyterminal (A,B), GRP aminoterminal (C,D), and GRP(1–16) carboxyterminal (E,F) immunoreactivity in guinea pig (A,C,E) and rat brain (B,D,F) are shown. The column was calibrated with (a) $^{125}$I-GRP, MW=2800, (b) $^{125}$I-α-melanocyte stimulating hormone, MW=1770, (c) $^{125}$I-met-enkephalin-Arg$^6$-Phe$^7$, MW=880).

Referring to FIG. 2, the RP-HLC profiles of the lower MW GRP immunoreactive peaks from gel filtration of guinea pig and rat brain are shown. Profile (A) is the GRP aminoterminal immunoreactive peak and Profile (A') is the GRP(1–16) carboxyterminal immunoreactive peak from guinea pig gel filtration fractions 48,49,50. Profile (B) is the GRP(1–16) carboxyterminal immunoreactive peak from rat brain gel filtration fractions 48,49,50. Profiles C and D are the GRP carboxyterminal immunoreactive peaks from gel filtration fractions 54,55,56 from guinea pig brain and rat brain, respectively. Chromatography was performed on an Altex Ultrasphere ODS column (250 mm×4.6 mm, particle size 5 μm). Two Altex HPLC pumps and a Beckman gradient mixing computer were used to generate an acetonitrile gradient of 0–17.5 percent in 5 minutes followed by a 17.5–35 percent gradient in 75 minutes. HPLC buffer consisted of 50 mM monosodium phosphate, 1 mg ml$^{-1}$ phosphoric acid and 5 percent methanol, pH 2.7. The flow rate was 1.25 ml min$^{-1}$ and 1 min fractions were collected. ~10,000 cpm of $^{125}$I-α-neo-endorphin and $^{125}$I-dynorphin were added as internal standards. Radioactivity in the eluate was monitored with a continuous flow through γ-counter (Isoflo, Nuclear Enterprises). The Markers (a)–(g) represent the position of the immunoreactive peaks of: (a) GRP(1–13), (b) GRP(18–27), (c) methionine sulfoxide bombesin, (d) bombesin, (e) GRP(1–16), (f) trypsinized bombesin, (g) GRP(1–27).

Referring to FIG. 3, the RP-HPLC profiles of the larger MW GRP immunoreactive peak from gel filtration of guinea pig and rat brain are shown. Profile (A) is the immunoreactive peak of GRP aminoterminal and Profile (A') is the immunoreactive peak of GRP carboxyterminal from guinea pig brain gel filtration fractions 39,40,41. Profile (C) represents the GRP aminoterminal immunoreactivity and Profile (C') GRP carboxyterminal immunoreactivity of trypsin digested guinea pig gel filtration fractions 39,40,41. Profile (D) represents GRP carboxyterminal immunoreactivity of trypsin digested rat brain gel filtration fractions 39,40,41. The Markers (a)–(g) represent the position of the immunoreactive peaks of: (a) GRP(1–13), (b) GRP(18–27), (c) methionine sulfoxide bombesin, (d) bombesin, (e) GRP(1–16), (f) trypsinized bombesin, (g) GRP(1–27).

In gel filtration of guinea pig brain extract, two peaks of GRP carboxyterminal immunoreactivity were observed (FIG. 1A). The large molecular weight (MW) peptide had an identical size and RP-HPLC retention time as porcine GRP(1–27) (FIG. 3A'). Upon trypsin digestion this material liberated an equimolar amount of a peptide which co-chromatographed with GRP(18–27) (FIG. 3C'). The smaller MW peak of GRP carboxyterminal immunoreactivity had an identical size and RP-HPLC retention time as GRP(18–27) (FIG. 2C).

Upon gel filtration chromatography of guinea pig brain extracts, the GRP aminoterminal RIA recognized two peaks of immunoreactivity (FIG. 1C). The large MW peptide had an identical size and RP-HPLC retention time as GRP(1–27) (FIG. 3A). The GRP aminoterminal and carboxyterminal RIA's measured equimolar amounts of this material, the GRP(1–16) carboxyterminal RIA did not recognize this material. Upon trypsin digestion of this material, the GRP aminoterminal RIA recognized an equimolar amount of material which co-chromatographed with GRP(1–13) (FIG. 3C). The smaller MW material had a similar size and RP-HPLC retention time as GRP(1–16) (FIG. 2A). In both gel filtration and RP-HPLC this peak of immunoreactivity was detected in approximately equimolar amounts by the GRP carboxyterminal RIA (FIGS. 1E, 2A').

These results demonstrate the presence in guinea pig brain of a GRP(1-27)-like peptide, and the GRP(1-16) and GRP(18-27)-like peptides of the present invention.

In gel chromatographs of rat brain, the GRP carboxyterminal RIA revealed two peaks of immunoreactivity (FIG. 1B). The larger MW peak had a size similar to GRP(1-27), however, in RP-HPLC this material eluted several minutes earlier than GRP(1-27) (FIG. 3B). Upon trypsin digestion an equimolar amount of a peptide which co-chromatographed with GRP(18-27) was formed (FIG. 3D). The smaller MW peak had a similar size and retention time as GRP(18-27) (FIG. 2D).

The GRP aminoterminal RIA revealed no peaks of immunoreactivity (FIG. 1D). The GRP(1-16) carboxyterminal RIA identified a single peak of immunoreactivity of similar size as GRP(1-16) (FIG. 1F). On RP-HPLC this material eluted several minutes earlier than GRP(1-16) (FIG. 2B).

These results demonstrate the presence in rat brain of a GRP(18-27)-like peptide of similar size and RP-HPLC retention time as GRP(18-27).

EXAMPLE 2

Synthesis of GRP(1-16) and (18-27)-Like Peptides

The GRP(1-16)-like peptide and the GRP(18-27)-like peptide were synthesized on benzhydrylamine resin (0.5 mmole/g), according to the procedures of Matsueda et al., *Peptides* 2 45-50 (1981). The peptides were cleaved from the resin and purified by partition chromatography on Sephadex G-25. The purity was confirmed by thin layer chromatography and reverse phase high performance liquid chromatography. Amino acid analysis further confirmed the correct composition. All amino acids used, except Gly, were of the L-configuration.

The GRP-like peptides of the present invention, GRP(1-16)-like peptide and GRP(18-27)-like peptide, and their pharmaceutically acceptable salts are useful for lowering body temperature in mammals; increasing respiratory activity in mammals, including increasing respiratory rate and volume; reducing food intake or suppressing appetite; stimulating pancreatic hormone release in mammals, including insulin, glucagon, neurotensin and gastrin; stimulating pituitary hormone release in mammals, including prolactin, growth hormone and lutenizing hormone; and suppressing thyroid hormone release in mammals.

The GRP-like peptides of the present invention may be admixed with conventional pharmaceutical carriers, such as saline, or may be formed into pellets, capsules, and the like. Preferably, the GRP-like peptide of the present invention will be administered intraveneously.

What is claimed is:

1. A biologically pure polypeptide having the formula Ala-Pro-Val-Ser-Val-Gly-Gly-Gly-Thr-Val-Leu-Ala-Lys-Met-Tyr-Pro-NH$_2$.

2. A biologically pure polypeptide having the formula Gly-Asn-His-Trp-Ala-Val-Gly-His-Leu-Met-NH$_2$.

3. A method for lowering body temperature in a mammal comprising the step of administering to said mammal an effective amount of a compound having the formula Ala-Pro-Val-Ser-Val-Gly-Gly-Gly-Thr-Val-Leu-Ala-Lys-Met-Tyr-Pro-NH$_2$.

4. A method for lowering body temperature in a mammal comprising the step of administering to said mammal an effective amount of a compound having the formula Gly-Asn-His-Trp-Ala-Val-Gly-His-Leu-Met-NH$_2$.

5. A method for increasing respiratory activity in a mammal comprising the step of administering to said mammal an effective amount of a compound having the formula Ala-Pro-Val-Ser-Val-Gly-Gly-Gly-Thr-Val-Leu-Ala-Lys-Met-Tyr-Pro-NH$_2$.

6. A method for increasing respiratory activity in a mammal comprising the step of administering to said mammal an effective amount of a compound having the formula Gly-Asn-His-Trp-Ala-Val-Gly-His-Leu-Met-NH$_2$.

7. A method for reducing food intake in a mammal comprising the step of administering to said mammal an effective amount of a compound having the formula Ala-Pro-Val-Ser-Val-Gly-Gly-Gly-Thr-Val-Leu-Ala-Lys-Met-Tyr-Pro-NH$_2$.

8. A method for reducing food intake in a mammal comprising the step of administering to said mammal an effective amount of a compound having the formula Gly-Asn-His-Trp-Ala-Val-Gly-His-Leu-Met-NH$_2$.

9. A method for stimulating pancreatic hormone release in a mammal comprising the step of administering to said mammal an effective amount of a compound having the formula Ala-Pro-Val-Ser-Val-Gly-Gly-Gly-Thr-Val-Leu-Ala-Lys-Met-Tyr-Pro-NH$_2$.

10. A method for stimulating pancreatic hormone release in a mammal comprising the step of administering to said mammal an effective amount of a compound having the formula Gly-Asn-His-Trp-Ala-Val-Gly-His-Leu-Met-NH$_2$.

11. A method for stimulating pituitary hormone release in a mammal comprising the step of administering to said mammal an effective amount of a compound having the formula Ala-Pro-Val-Ser-Val-Gly-Gly-Gly-Thr-Val-Leu-Ala-Lys-Met-Tyr-Pro-NH$_2$.

12. A method for stimulating pituitary hormone release in a mammal comprising the step of administering to said mammal an effective amount of a compound having the formula Gly-Asn-His-Trp-Ala-Val-Gly-His-Leu-Met-NH$_2$.

13. A method for suppressing thyroid hormone release in a mammal comprising the step of administering to said mammal an effective amount of a compound having the formula Ala-Pro-Val-Ser-Val-Gly-Gly-Gly-Thr-Val-Leu-Ala-Lys-Met-Tyr-Pro-NH$_2$.

14. A method for suppressing thyroid hormone release in a mammal comprising the step of administering to said mammal an effective amount of a compound having the formula Gly-Asn-His-Trp-Ala-Val-Gly-His-Leu-Met-NH$_2$.

15. A pharmaceutical composition comprising an amount of the polypeptide defined in claim 1 effective to lower body temperature to increase respiratory activity, to suppress appetite, to stimulate pancreati hormone release to stimulate pituitary hormone release or the suppress thyroid hormone release in mammals, or a pharmaceutically acceptable salt thereof, in a pharmaceutically acceptable carrier.

16. A pharmaceutical composition comprising an amount of the polypeptide defined in claim 2 effective to lower body temperature to increase respiratory activity, to suppress appetite, to stimulate pancreati hormone release to stimulate pituitary hormone release or the suppress thyroid hormone release in mammals, or a pharmaceutically acceptable salt thereof, in a pharmaceutically acceptable carrier.

* * * * *